(12) United States Patent
Lin et al.

(10) Patent No.: US 9,521,851 B2
(45) Date of Patent: Dec. 20, 2016

(54) METHOD OF FABRICATING ANTIMICROBIAL COMPLEX SURFACE

(71) Applicant: CATCHER TECHNOLOGY CO., LTD., Tainan (TW)

(72) Inventors: Chung-Cheng Lin, Taichung (TW); Feng-Ju Lai, Taipei (TW)

(73) Assignee: CATCHER TECHNOLOGY CO., LTD., Tainan (TW)

( * ) Notice: Subject to any disclaimer, the term of this patent is extended or adjusted under 35 U.S.C. 154(b) by 0 days.

(21) Appl. No.: 14/848,821

(22) Filed: Sep. 9, 2015

(65) Prior Publication Data

US 2015/0373988 A1 Dec. 31, 2015

Related U.S. Application Data

(62) Division of application No. 14/230,874, filed on Mar. 31, 2014, now Pat. No. 9,332,765.

(51) Int. Cl.
*A01N 59/16* (2006.01)
*C09D 5/14* (2006.01)
*C25D 11/24* (2006.01)

(52) U.S. Cl.
CPC ............... *A01N 59/16* (2013.01); *C09D 5/14* (2013.01); *C25D 11/246* (2013.01)

(58) Field of Classification Search
CPC .......... A01N 59/16; C25D 11/246; C09D 5/14
See application file for complete search history.

(56) References Cited

U.S. PATENT DOCUMENTS 6,379,523 B1 * 4/2002 Takabayashi .......... C25D 11/08
205/173

FOREIGN PATENT DOCUMENTS

JP 10280191 A * 10/1998

* cited by examiner

*Primary Examiner* — Gina Justice
(74) *Attorney, Agent, or Firm* — Li & Cai Intellectual Property (USA) Office

(57) ABSTRACT

A method of fabricating an antimicrobial metal complex surface, and the method includes providing an article, and the article has a first metal complex surface treated by anodization. The first metal complex surface is formed with a first pore. Secondly a silver suspension is provided. The silver suspension also has pore sealing agent. The article is soaked in the suspension to form a pore sealing layer having silver particles on the first metal complex surface such that the silver particles are distributed in the pore sealing layer. The antimicrobial metal complex surface fabricated by the method inhibits microorganism growth on the anodized metal surface.

12 Claims, 4 Drawing Sheets

METHOD OF FABRICATING ANTIMICROBIAL COMPLEX SURFACE

CROSS REFERENCE TO RELATED APPLICATIONS

This application is a divisional application of Ser. No. 14/230,874 filed on Jan. 19, 2012, entitled "ANTIMICROBIAL COMPLEX SURFACE AND METHOD OF FABRICATING THE SAME", the entire disclosures of which are incorporated herein by reference.

BACKGROUND

1. Field of the Invention

The instant disclosure relates to a method of fabricating an antimicrobial complex surface; in particular, to a method of fabricating an antimicrobial complex surface which a complex surface that has undergone anodization to inhibit microorganism growth thereon.

2. Description of Related Art

In general, metal anodization refers to a technique to electrolysis the aluminum and the alloy of aluminum and form a conversion coating on the surface. It is also known as aluminum anodization. The surface treated by aluminum anodization is corrosion resistance, paint adhesion, electrical insulation and abrasion resistance. The aluminum oxidize layer has many micropores. Therefore the aluminum anodization is widely used to fabricate the outer case surface of the conventional electronic products, household appliance, furniture and daily goods.

However, portable 3C products, for example, the case of a mobile phone, handle of an object or ATM buttons can easily attract bacteria or microorganism because of constant contact with human body. *Staphylococcus aureus* (*S. aureus*) on human skin and *Escherichia coli* (*E. coli*) remaining on the hands because of not well cleaning are usually seen on the device above. Therefore the surface undergoing aluminum anodization becomes media spreading bacteria, microorganism or even pathogen. However, to treat the anodized aluminum surface with antibacterial or antimicrobial treatment shows very little effect or may compromise the existing advantageous property of the anodized aluminum surface. The reason of ineffective treatment may lie on the antimicrobial material not being properly formed or distributed on the surface. Furthermore, when the antimicrobial material is at presence, the coloring is weakened.

To address the above issues, the inventor strives via associated experience and research to present the instant disclosure, which can effectively improve the limitation described above.

BRIEF SUMMARY OF THE INVENTION

The instant disclosure provides an antimicrobial complex surface and method of fabricating the same to inhibit microorganism growth on a complex surface of any products. Also, the instant disclosure maintains the existing advantages of the complex surface when, at the same time, the complex surface can suppress the activity of microorganism.

According to one exemplary embodiment of the instant disclosure, a method of fabricating the antimicrobial complex surface is provided. The method includes providing an article, and the article has a first metal complex surface treated by anodization. The first metal complex surface is formed with a first pore. Secondly a silver suspension is provided. The silver suspension also has pore sealing agent. The article is soaked in the suspension to form a pore sealing layer having silver particles on the first metal complex surface such that the silver particles are distributed in the pore sealing layer.

According to another embodiment of the instant disclosure, an antimicrobial complex surface to form on the surface of an article. The antimicrobial complex surface includes a first metal complex surface treated by anodization. The first metal complex surface is disposed on the surface of the article according to a first distribution area. The first metal complex surface is formed with a first pore. The antimicrobial complex surface further includes a pore sealing layer having a plurality of silver particles and disposed on the first metal complex surface to fill in the first pore.

In summary, when the first pore of the first metal complex surface is sealed, the silver particles are distributed in the first pore and the pore sealing layer, such that the metal complex surface exhibits great antimicrobial activity and its existing property is not affected.

In order to further understand the instant disclosure, the following embodiments are provided along with illustrations to facilitate the appreciation of the instant disclosure; however, the appended drawings are merely provided for reference and illustration, without any intention to be used for limiting the scope of the instant disclosure.

DETAILED DESCRIPTION OF THE INVENTION

The aforementioned illustrations and following detailed descriptions are exemplary for the purpose of further explaining the scope of the instant disclosure. Other objectives and advantages related to the instant disclosure will be illustrated in the subsequent descriptions and appended drawings.

Figure 1A:
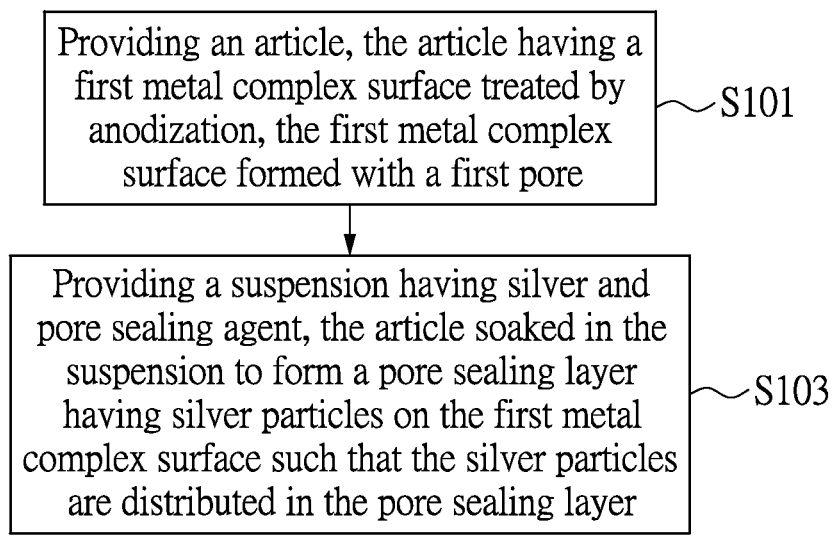
FIG. 1A is a flow chart describing a method of fabricating an antimicrobial complex surface of the instant disclosure.

Please refer to FIG. 1A showing a flow chart of method of fabricating an antimicrobial complex surface of the instant disclosure. The steps are described hereinafter.

Figure 2A:
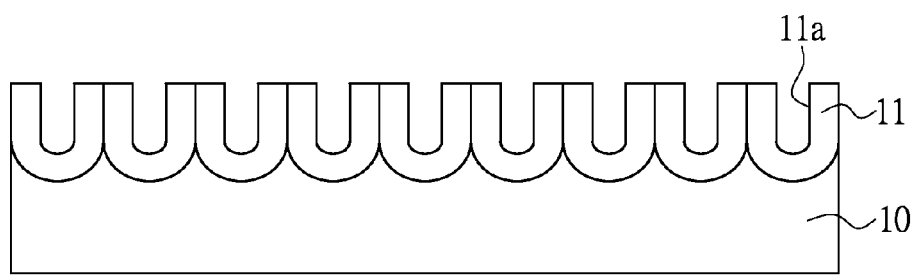
FIGS. 2A to 2D are schematic diagrams of a process showing a cross-sectional view of an antimicrobial complex surface fabricated by a method of the instant disclosure.

Step S101: Please refer to FIG. 2A showing a schematic diagram of a cross-sectional view of the antimicrobial complex surface fabricated by the method of the instant disclosure. An article 10 is provided. The article 10 may be conventional processed article, for example, shell of a mobile phone. Mostly the article is made of aluminum or aluminum alloy yet it is not limited thereto. The article 10 has a first metal complex surface 11 treated by anodization. Preferably, the first metal complex surface 11 is disposed on the article 10 according to a first distribution area. After anodization, the first metal complex surface 11 is formed with a first pore 11a. In addition, the first metal complex surface 11 undergoes anodization, and therefore the first metal complex surface 11 is equivalent to a conversion coating. Furthermore, the first pore 11a may be formed on an upper surface (not labeled) of the article 10 or a lower surface (not labeled). In the instant embodiment, the pore is formed on the upper surface as an example, and the instant disclosure is not limited thereto. Preferably, the article 10 may have specific configuration according to desire requirement. The article 10 may be pre-processed by machines or preferably by computer numerical control (CNC). The processing may further includes a surface visual effect treatment. It should also be noted that before anodizing, a pre-treatment can be conducted to the article 10. The pre-treatment (not limited hereto) may include degreasing, alkaline etching, first pickling, chemical polishing and second pickling or the like. The cycle number of the sub procedure depends on the final quality required. After each procedure, it includes at least once water rinse. The cycle of water rinse may one to five, preferably two to remove any remaining chemical agent or impurities. The parameters of each procedure may be adjusted according to the requirement of the article 10, and they are not limited thereby. In other words, the article 10 of the instant disclosure may undergo the abovementioned pre-treatment and the way or parameter is not limited thereto.

Figure 2B:
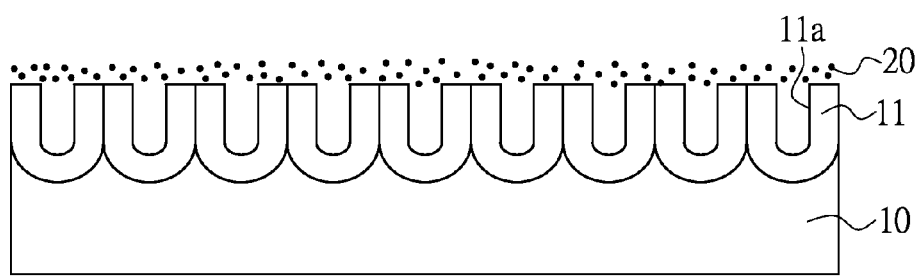
Figure 2C:
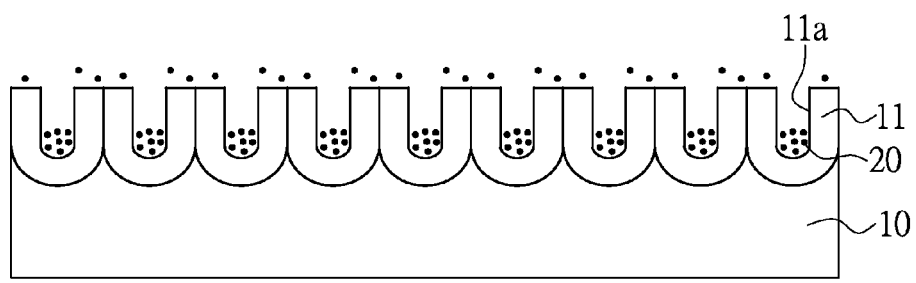

Step 103: Please refer to FIG. 2B showing a schematic diagram of a cross-sectional view of the antimicrobial complex surface fabricated by the method of the instant disclosure. A suspension having silver (not shown) is provided. The silver suspension is mixed with a pore sealing agent to form a fabricated solution. That is to say the silver suspension is the fabricated solution, a suspension mixed with silver particles and pore sealing agent. The article 10 is deposited in the silver suspension, such that the silver particles 20 can adhere to the first metal complex surface 11 of the article 10. Moreover, after anodizing, the first metal complex surface 11 and the pore 11a are slightly positively charged. When the silver particles 20 are electrically neutral, the silver suspension can still be mixed and have an anionic surfactant. The anionic surfactant occupies a first percentage by weight in the silver suspension. The first percentage by weight may be larger than 0 and below 8%. The anionic surfactant may further coat the silver particles 20 as in a liquid state, resulting in slightly negatively charged silver particles 20. Compared to the previously mentioned silver particles 20, the negatively charged silver particles 20 are easier to adhere to the first metal complex surface 11. As the time of the article 10 soaked in the silver suspension increases and the temperature increase to 80 to 100 Celsius degrees, the number of silver particles 20 attached to the first metal complex surface 11 of the article 10 will be higher. The soaking time is preferably between 10 to 60 minutes. Preferably, the anionic surfactant may be sodium dodecylbenzenesulfonate or sodium dodecyl sulfate (SDS) or the like.

Accordingly, the pore sealing agent forms a pore sealing layer 12 on the first metal complex surface 11 with the silver particles 20 in composite, such that the silver particles are distributed in the pore sealing layer 12. In this step, the pore sealing agent is preferably a nickel acetate pore sealing agent. In other words, the pore sealing layer 12 may be a type of pore sealing nickel layer. It should be noted that because of the addition of the pore sealing agent and in the process of the formation of the pore sealing layer 12, the silver particles 20 attached to the first metal complex surface 11 in advance in the step S103 can mix again into the pore sealing layer 12 and precipitate on the first metal complex surface 11 with the pore sealing layer 12. By X-ray fluorescence (XRF), the percentage by weight of the silver particles 20 in the pore sealing layer 12 may be 0.01% to 0.2%.

Figure 1B:
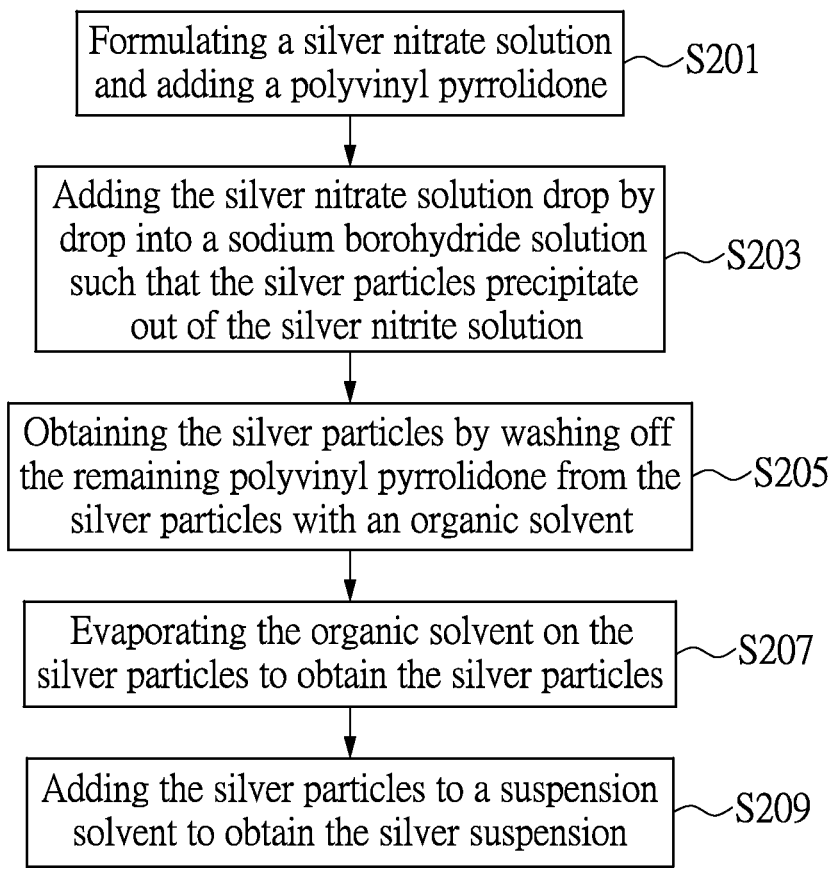
FIG. 1B is a flow chart describing a preparation of a nano-silver solution of a method of fabricating an antimicrobial complex surface of the instant disclosure.

Furthermore, please refer to FIG. 1B showing a flow chart of making a silver suspension according to the method of fabricating the antimicrobial complex surface. The silver suspension is obtained from a method of preparing silver suspension including the following steps.

Step S201: a silver nitrate solution is formulated. The molar concentration of the silver nitrate solution may be 0.01M to 0.1M. Preferably, for example, the starting concentration of the silver nitrate solution may be 0.01172M (e.g., 0.36 g silver nitrate and 108 ml water). Next, polyvinyl pyrrolidone (PVP) is added to the silver nitrate solution, and the percentage by weight of PVP in the silver nitrate solution may fall between 0.027% and 0.054%. Therefore the concentration of silver nitrate solution should not exceed 0.01172M. The concentration of the drugs and agent should not be too high, or otherwise the silver will overly aggregate and the diameter becomes too large.

Step S203: The silver nitrate solution is added to the $NaBH_4$ solution drop by drop. The molar concentration of $NaBH_4$ in the $NaBH_4$ solution ranges from 0.00846M to 0.01M. For example, the $NaBH_4$ solution can be prepared by adding 0.16 g of $NaBH_4$ to 500 ml water, and the instant disclosure is not limited thereto. The nano silver particles gradually precipitate out of the silver nitrate solution. It is important to add the solution "drop by drop", such that when the silver particles precipitate, the silver particles do not precipitate in a short time which leads to silver particles aggregation, and the precipitated silver particles have smaller diameter. To ensure smaller silver particles precipitate, in the step of adding silver nitrate solution drop by drop to the $NaBH_4$ solution, it can be conducted under 13 Celsius degree or preferably below 10 Celsius degree and above 4 Celsius degree. The low temperature reduces the rate of silver particle precipitation to effectively avoid too many silver particles to aggregate in a given time frame which leads to undesired large silver particles.

Step S205: The silver particles are obtained by filtering and washed by organic solvent to remove any remaining PVP. The organic solvent may be alcohol, for example, methanol or ethanol. Step S207: The silver particles washed by organic solvent still have remaining organic solvent, and therefore the evaporation of the organic solvent can be facilitated by reduced pressure distillation. The organic solvent cannot be completely evaporated, or otherwise the silver particle will aggregate excessively and the diameter becomes too large. Step S209: The silver particles are then added to a suspension solvent to obtain the silver suspension. The silver particles in the silver suspension obtained from the abovementioned method are nano-sized silver particles (silver particles 20 in FIGS. 2A to 2D) whose diameter ranges between 10 and 500 nm.

Figure 2D:
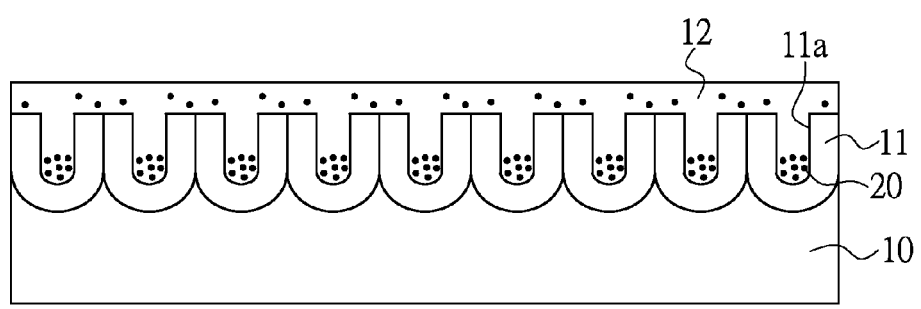

Please refer to FIGS. 1A and 2D. Preferably, the anodized first metal complex surface 11 may undergo at least once coloration. For example, the article 10 is soaked in an anodized solution having 20% to 25% of sulfuric acid. The voltage is set between 10 and 16 volt, the current density ranges between 0.8 and 2.0 $A/dm^2$, and the duration is less than 45 minutes. Preferable treatment duration is at least 30 minutes. After anodizing, the first metal complex surface 11 undergoes the first coloration. The first coloration may be attachment coloration or chemical coloration so as to allow the first metal complex surface 11 to be a first conversion film having a first color. Additionally, the first color is distributed on the first metal complex surface 11 and to the pore 11a of the first metal complex surface 11. Therefore, in the following step of pore sealing, the pore sealing layer 12 coats the first conversion film, and meanwhile the pore sealing layer 12 has silver particles.

The coloration may be split into multiple steps according to desired color type. IF another coloration is required, a portion of the first metal complex surface 11 (first conversion film) on the article 10 surface has to be removed (fro example, by CNC) so as to reveal the non-oxidized portion on the article 10, such that another anodizing can be done on the portion of the first metal complex surface 11 on the article 11 to form a second metal complex surface (not labeled). For example, the other anodizing can be conducted between 15 and 25 Celsius degree. The article 10 is soaked in the anodizing solution having 20 to 25% of sulfuric acid, the voltage falls at 6 to 25 volt, and the treatment duration is 1 to 20 minutes. After that, another coloration can be conducted, it can still be either attachment coloration or chemical coloration. The second metal complex surface of the article 10 has a second conversion film having a second color. Then the abovementioned step S103 may proceed.

Please refer to FIG. 2D and the abovementioned method. The instant disclosure further includes an antimicrobial complex surface to form on the surface of an article 10. The antimicrobial complex surface includes at least a first metal complex surface 11 treated by anodization. And a pore sealing layer 12. Preferably, the first metal complex surface 11 is distributed on the surface of the article 10 according to a first distribution area (not shown). Also, the first metal complex surface 11 is formed with a first pore 11a. The article 10 may be an aluminum or aluminum alloy processed article.

The pore sealing layer 12 has a plurality of silver particles 20 and is disposed on the first metal complex surface 11 to fill the first pore 11a. Preferably, the sealing pore layer 12 is formed by a nickel nitrate pore sealing agent. The treatment temperature may be 80 to 99 degree, and the treatment time can be 1 to 30 minutes. Finally, the article is baked to dry. In other words, the pre sealing layer 12 may be a pore sealing nickel layer. The first metal complex surface 11 may undergo coloration to show or have a first color.

Figure 3:
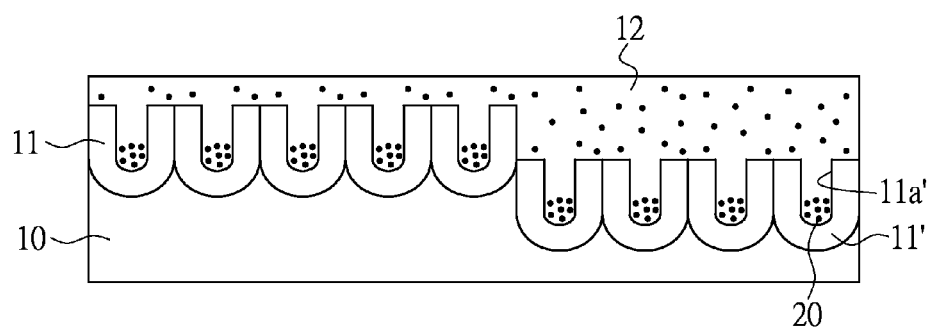
FIG. 3 is a cross-sectional view of an antimicrobial complex surface including a second metal complex surface close to the first metal complex surface.

Please refer to FIG. 3. Furthermore, the antimicrobial complex surface may include a second metal complex surface 11'. The second metal complex surface 11' is distributed on the surface of the article 10 according to a second distribution area and close to the first metal complex surface 11. In addition, the second complex surface 11' may be slightly lower than the first metal complex surface 11. Similar to the first metal complex surface 11, the second metal complex surface 11' may have a second pore 11'a, and the pore sealing layer 12 may also have the silver particles 20 on top of the second metal complex surface 11' to fill in the second pore 11'a. Likewise, the second metal complex surface 11' may show a second color.

After the surface of the article 10 is treated by the above mentioned method, the silver percentage by weight on its surface reaches 0.01% which satisfies the concentration of silver that exhibits antimicrobial activity according to SGS Taiwan Ltd. Experimental data related antimicrobial activity conducted by SGS also show the surface of the article after being treated can actually inhibit the activity of microorganisms. The results are shown in Table 1 and Table 2.

TABLE 1

Strain: *Staphylococcus aureus* (ATCC 6538P)

| Test Group | CFU/cm$^2$ | LOG | Bacterial Resistance (R) |
|---|---|---|---|
| A | 1.3 × 10$^4$ | 4.11 | >5.18 |
| B | 9.5 × 10$^4$ | 4.98 | |
| C | <0.63 | −0.2 | |

TABLE 2

Strain: *Escherichia coli* (ATCC 8739)

| Test Group | CFU/cm$^2$ | LOG | Bacterial Resistance (R) |
|---|---|---|---|
| A | 1.2 × 10$^4$ | 4.08 | >5.87 |
| B | 4.7 × 10$^5$ | 5.67 | |
| C | <0.63 | −0.2 | |

In Table 1, *Staphylococcus aureus* is used (strain code: ATCC6538P) for testing with Gram positive bacteria. In Table 2, *Escherichia coli* (strain code: ATCC8739) is sued for testing Gram negative bacteria. The test group A in Table 1 and 2 represents untreated article sample, the bacterial colony size is calculated by colony-forming unit/cm$^2$ (CFU/cm$^2$) right after seeded Test group B represents untreated article sample and the bacterial colony size is calculated after 24 hours of incubation. Test group C represents article treated by the method of the instant disclosure, and the bacterial colony size is calculated after 24 hours of incubation. The bacterial resistance (R) is derived from the logarithm of the value of B divided by the value of C. According to the SGS standard, if the bacterial resistance (R) is greater than 2.0, it shows the antimicrobial activity. The above data are obtained after three times of repetitions, and similar results are shown which suggest that the instant disclosure exhibit antimicrobial activity.

The descriptions illustrated supra set forth simply the preferred embodiments of the instant disclosure; however, the characteristics of the instant disclosure are by no means restricted thereto. All changes, alternations, or modifications conveniently considered by those skilled in the art are deemed to be encompassed within the scope of the instant disclosure delineated by the following claims.

What is claimed is:

1. A method of fabricating antimicrobial complex surface comprising:
    providing an article, the article having a first metal complex surface treated by anodization, the first metal complex surface formed with a first pore; and
    providing a suspension having silver and pore sealing agent, the article soaked in the suspension to form a pore sealing layer having silver particles on the first metal complex surface such that the silver particles are distributed in the pore sealing layer;
    wherein the silver suspension is prepared by the steps comprising:
    formulating a silver nitrate solution having a molar concentration between 0.01M to 0.1M, adding a polyvinyl pyrrolidone, such that the polyvinyl pyrrolidone having a percentage by weight ranging between 0.027% to 0.054% in relation to the silver suspension;
    adding the silver nitrate solution drop by drop into a sodium borohydride solution, the sodium borohydride solution having a molar concentration between 0.00846M to 0.01M, such that the silver particles precipitate out of the silver nitrite solution;

obtaining the silver particles by washing off the remaining polyvinyl pyrrolidone from the silver particles with an organic solvent; and evaporating the organic solvent on the silver particles and adding the pore sealing agent to make the silver suspension.

2. The method of fabricating antimicrobial complex surface according to claim 1, wherein the suspension having silver further includes an anionic surfactant, the anionic surfactant has a first percentage by weight in the silver suspension, and the first percentage by weight ranges between 0 to 8%.

3. The method of fabricating antimicrobial complex surface according to claim 2, wherein the anionic surfactant is sodium dodecylbenzene sulfonate or sodium dodecyl sulfate.

4. The method of fabricating antimicrobial complex surface according to claim 1, wherein the pore sealing agent is a nickel acetate pore sealing agent, such that the pore sealing layer is formed with a pore sealing nickel layer, the silver particles are distributed in the pore sealing nickel layer.

5. The method of fabricating antimicrobial complex surface according to claim 1, wherein in the step of adding the silver nitrate solution drop by drop into a sodium borohydride solution, the temperature is below 13 Celsius degree and above 4 Celsius degree.

6. The method of fabricating antimicrobial complex surface according to claim 1, wherein the organic solvent is methanol or ethanol.

7. The method of fabricating antimicrobial complex surface according to claim 1, wherein in the step of evaporating the organic solvent on the silver particles further includes reduced pressure distillation to facilitate the evaporation of the organic solvent.

8. The method of fabricating antimicrobial complex surface according to claim 1 further comprising effecting a first coloration on the first metal complex surface, such that the first metal complex surface shows a first color.

9. The method of fabricating antimicrobial complex surface according to claim 8 further comprising: removing a portion of the first metal complex surface, effecting anodization on the article where the first metal complex surface is not present to form a second metal complex surface, and effecting a second coloration, such that the pore sealing layer is formed on the surface of the second metal complex surface.

10. The method of fabricating antimicrobial complex surface according to claim 9, wherein the coloring is attachment coloring or chemical coloring.

11. A method of fabricating antimicrobial complex surface comprising:

providing an article, the article having a first metal complex surface treated by anodization, the first metal complex surface formed with a first pore;

providing a suspension having silver and pore sealing agent, the article soaked in the suspension to form a pore sealing layer having silver particles on the first metal complex surface such that the silver particles are distributed in the pore sealing layer;

effecting a first coloration on the first metal complex surface, such that the first metal complex surface shows a first color; and removing a portion of the first metal complex surface, effecting anodization on the article where the first metal complex surface is not present to form a second metal complex surface, and effecting a second coloration, such that the pore sealing layer is formed on the surface of the second metal complex surface.

12. The method of fabricating antimicrobial complex surface according to claim 11, wherein the coloring is attachment coloring or chemical coloring.

* * * * *